United States Patent [19]
Anderson

[11] 3,982,903
[45]*Sept. 28, 1976

[54] ALKYLATION REACTION CHAMBER

[75] Inventor: Robert F. Anderson, La Grange Park, Ill.

[73] Assignee: Universal Oil Products Company, Des Plaines, Ill.

[ * ] Notice: The portion of the term of this patent subsequent to Oct. 21, 1992, has been disclaimed.

[22] Filed: July 14, 1975

[21] Appl. No.: 595,839

Related U.S. Application Data

[63] Continuation-in-part of Ser. No. 462,071, April 18, 1974, Pat. No. 3,914,111.

[52] U.S. Cl. ............................. 23/288 E; 23/283; 23/285; 23/288 K; 23/289; 260/683.48
[51] Int. Cl.² ..................... B01J 1/00; B01J 8/08; C07C 3/54
[58] Field of Search ................. 23/288 E, 283, 285, 23/289; 260/683.48

[56] References Cited
UNITED STATES PATENTS

| | | |
|---|---|---|
| 3,150,934 | 9/1964 | Hazard .............................. 23/285 X |
| 3,322,411 | 5/1967 | Moore .............................. 23/285 X |
| 3,435,092 | 3/1969 | Hutson, Jr. et al. ........... 260/683.43 |
| 3,914,111 | 10/1975 | Anderson .......................... 23/288 E |

*Primary Examiner*—Joseph Scovronek
*Attorney, Agent, or Firm*—James R. Hoatson, Jr.; Robert W. Erickson; William H. Page, II

[57] ABSTRACT

An improved alkylation reaction chamber for contacting acid catalysts with alkylation reactants. A heat exchanger, a plurality of baffles and a plurality of spray nozzle assemblies are disposed within a vertically positioned, elongated vessel. Acid catalyst flows upward in serpentine fashion through the vessel and alkylation reactants are sprayed into the catalyst at a plurality of elevations within the vessel. Sprays are directed in substantially all directions so that maximum utilization of the available reaction chamber volume is effectuated. Exothermic heat of reaction is removed by the heat exchanger.

3 Claims, 1 Drawing Figure

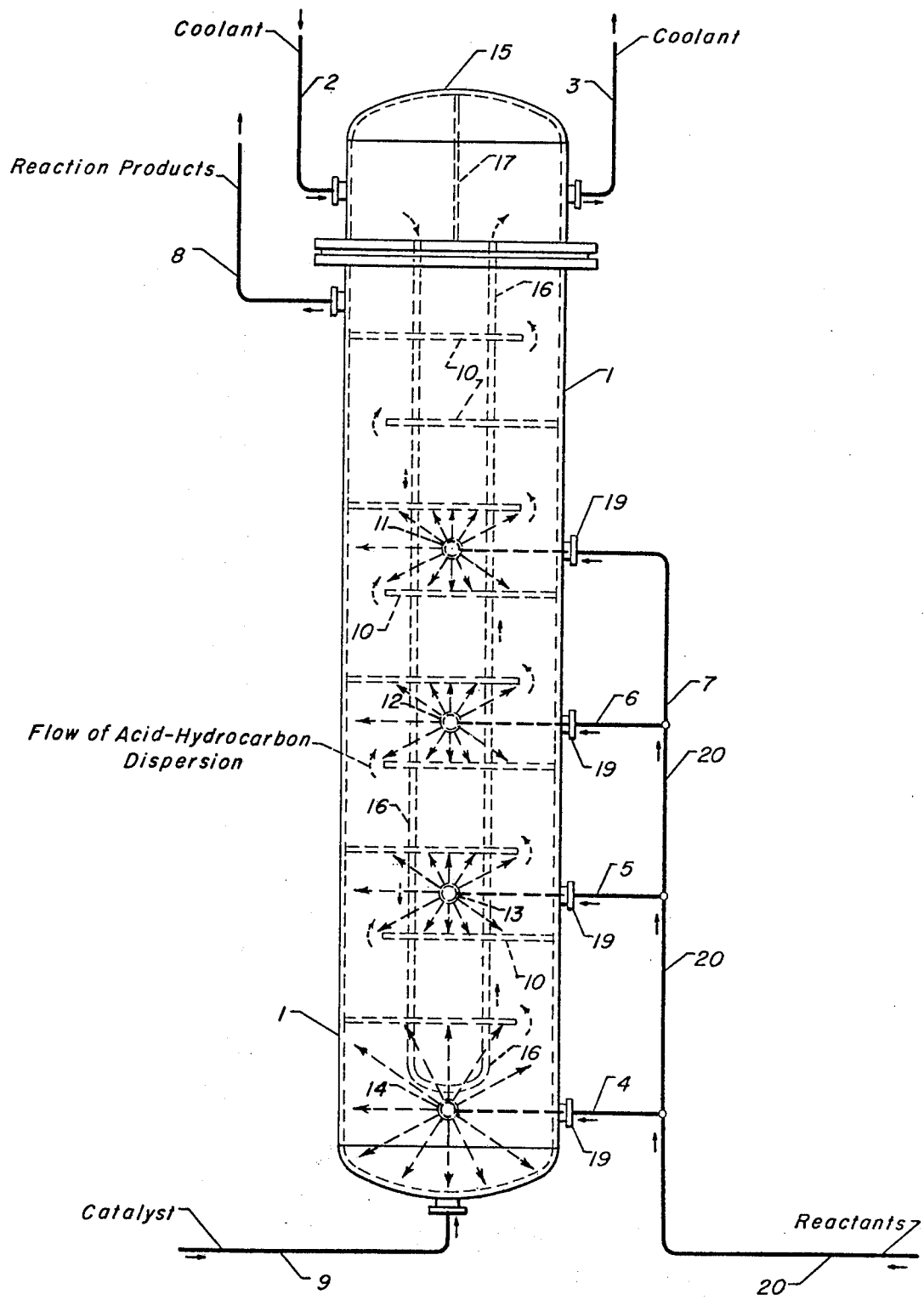

ALKYLATION REACTION CHAMBER

CROSS-REFERENCE TO RELATED APPLICATION

This application is a continuation-in-part of my copending application Ser. No. 462,071 which was filed on Apr. 18, 1974, now U.S. Pat. No. 3,914,111, issued Oct. 21, 1975.

BACKGROUND OF THE INVENTION

1. Field of the Invention

The field of art to which this invention pertains is that of hydrocarbon processing. In particular, this invention relates to a reactant-contacting apparatus useful for liquid phase alkylation utilizing hydrofluoric acid as the catalyst.

2. Prior Art

Efficiency in the use of petroleum as an energy source has recently become vastly more important than ever before, due primarily to supply restrictions originating in petroleum exporting countries. A contribution to more efficient use may be made in an alkylation process by providing higher product quality through an improved reactant contacting apparatus.

The advantage in using spray nozzles to create fine dispersions of reactant droplets sprayed into a moving catalyst phase is well known in the art. Exemplary of designs of this type are U.S. Pat. Nos. 3,560,587; 3,607,970 and 3,707,580. These references, however, do not disclose the benefit to be gained by the use of a reaction chamber which provides not only improved and prolonged dispersion of hydrocarbon reactants into the alkylation catalyst but also maximum utilization of the internal space within the reaction chamber. The present invention improves product quality by providing such a reaction chamber.

OBJECTS AND EMBODIMENTS

It is an object of this invention to provide a method for improving the product of an acid catalyzed alkylation process. Another object of this invention is to provide a novel alkylation apparatus for improved contact of reactants and catalyst in an acid-catalyzed alkylation process.

In one embodiment, my invention affords an acid-catalyzed alkylation reaction chamber which comprises, in combination: (a) a vertically-disposed, elongated cylindrical vessel having internal heat removal means; (b) an acid inlet port at the lower end of said vessel and a reaction product outlet port at the upper end of said vessel; (c) a plurality of vertically spaced reactant stream inlet ports disposed along said vessel between said acid inlet port and said reaction product outlet port; (d) a plurality of vertically spaced baffles within said vessel perpendicular to the longitudinal axis thereof, said baffles dividing the inner volume of said vessel into compartments, and said baffles having circular segment-shaped openings at alternate sides of said vessel to provide a serpentine flow of liquid upwardly through the vessel; and (e) a plurality of reactant injection assemblies within said vessel, each disposed between a pair of adjacent baffles, within a compartment, and communicating with one of said reactant stream inlet ports, said injection assemblies comprising spray nozzles oriented to direct spray into substantially all portions of said compartment in which said injection assembly is situated.

BRIEF SUMMARY OF THE INVENTION

My invention involves a reaction chamber which provides prolonged and improved contact between hydrocarbon reactants and catalyst in an acid-catalyzed alkylation process. The reaction chamber may comprise a vertically-disposed, elongated chamber having at the lower end an acid inlet and, at the upper end, a reaction product outlet. The chamber has internally-placed heat exchange means for removal of exothermic heat of reaction, and disposed between the inlet and outlet are interposed pluralities of baffle means and reactant inlet means. These reactant inlet means comprise assemblies of spray nozzles. Acid flows upward in serpentine fashion through the chamber and reactants are introduced from each of the inlet means through its nozzles. Each assembly of spray nozzles emits spray in substantially all directions. The hydrocarbon sprays create a fine dispersion of the hydrocarbon and acid phases. The upward movement of the dispersion and the juxtaposition of baffle and reactant inlet means retard separation of the phases, thereby prolonging and improving contact between acid and reactants. Improved product qualities are obtained by virtue of the prolonged and improved contact between catalyst and reactants.

BRIEF DESCRIPTION OF THE DRAWING

A preferred embodiment of my invention is described in the attached drawing. This drawing is not intended to unduly limit the scope of my claims but is presented as a guide to understanding the invention.

The single FIGURE of the drawing is an elevation view of a reaction chamber consisting of vessel 1, having end section 15.

Vessel 1 is shown as a vertically positioned, elongated, enclosed cylinder. Coolant enters end section 15 through conduit 2 and, being restrained by baffle 17, passes through heat exchange means 16 and exits end section 15 through conduit 3. Heat exchange means 16 are shown schematically and may comprise a plurality of tubes or coils disposed within the reaction chamber. A cooling medium such as water is introduced into conduit 2 at a rate sufficient to maintain a predetermined temperature within the reaction chamber. An acid catalyst phase enters vessel 1 through conduit 9 and, being diverted by baffle means 10, passes in serpentine fashion through reaction chamber 1, exiting in conduit 8. Baffle means 10 are shown disposed within vessel 1 in planes perpendicular to the longitudinal axis of the reaction chamber. The baffle means are substantially evenly spaced between catalyst inlet 9 and reaction product outlet 8, and have circular segment-shaped openings at alternate sides of reaction chamber 1 such that flow of the catalyst phase therein is diverted from side to side in the aforementioned serpentine fashion. Reactants in conduit 20 pass into conduits 4,5,6, and 7 from which they enter through reactant stream inlet ports 19 into reactant injection assemblies 14,13,12 and 11, respectively. Reactants are sprayed into the acid catalyst phase through spray nozzles mounted in the reactant injection assemblies. Spray nozzles produce a fine dispersion of the reactants within the catalyst phase. Thereafter, reactants and reaction products are carried with the flow of the catalyst phase and exit vessel 1 in conduit 8.

DETAILED DESCRIPTION OF THE INVENTION

In the alkylation processes suitable for the use of my invention reactants ideally combine to yield, as a principal product, a hydrocarbon of carbon content equal to the sum of the carbon atoms of the olefin and alkylatable reactants, commonly known as mono-alkylate. A suitable alkylatable reactant may be a paraffinic hydrocarbon having a tertiary carbon atom such as isobutane or higher homologs of isobutane such as 2-methylbutane, 2-methylpentane, etc. Other useful alkylatable reactants include benzene, toluene, xylene, naphthenes, phenols, cresols, amines and the like.

The olefin reactants which may suitably be used in my invention include $C_3$-$C_{20}$ olefinic hydrocarbons, alkyl halides, alcohols, alkyl sulfates, alkyl phosphate, etc. Mono-olefins are preferable, such as propene and butenes.

Alkylation of the paraffinic reactant with the olefin is effected in the presence of an acid catalyst. Suitable catalysts include hydrogen halides, mineral acids such as phosphoric acid, Friedel-Crafts metal halides such as aluminum chloride, boron fluoride, etc. A preferred hydrogen fluoride catalyst contains approximately 70–90% hydrogen fluoride, organic material and less than 2% water.

Alkylation reaction conditions, to be maintained within the reaction chamber of the present invention, include a temperature of from about 0°F to about 150°F and a pressure of from about 1 atmosphere to about 40 atmospheres. The reaction temperature is one of the more important variables as it has a significant influence on the quality of the alkylate product. A preferred range of temperature is from about 80°F to about 100°F. Pressure is not a significant variable with respect to product quality, provided that it is sufficient to keep all hydrocarbon and acid catalyst in the liquid state. The volumetric ratio of acid catalyst to hydrocarbon within the reaction cooler is maintained within the range of 0.5:1 to 2:1. At some point below 0.5:1 process efficiency decreases for many reasons, among which are occurrence of undesirable reactions, and non-completion of desirable reactions. There appears to be no alkylate yield or quality improvement in increasing this ratio above 2:1. It is desirable to maintain a high ratio of the molar concentration of isoparaffin or aromatic present to the molar concentration of olefin present in order to produce high quality mono-alkylate. A broad range of this ratio is from about 6:1 to about 20:1 with a preferred operating range being from about 8:1 to about 16:1.

The essence of my invention involves the manner in which reactants are contacted with acid catalyst. It is well known in the art that intimate contact between the acid and hydrocarbon phases is required to produce a high quality alkylate product. In modern plants this contact is generally provided by dispersing the hydrocarbon into the acid phase using spray nozzles. The resulting dispersion is inherently unstable because of the immiscibility of the acid and hydrocarbon phases and because of their different densities. This presents a problem, because it is desirable that the phases remain dispersed during their passage through the alkylation reaction chamber.

The advent of horizontal reaction chambers having multiple points of injecton of hydrocarbon into acid represented a significant breakthrough in alkylation dispersion technology. However, in a horizontal reaction chamber the lighter phase tends to move upward and accumulate at the top as it passes through the chamber. This results in agglomerations of the lighter phase at the top of the chamber and the heavier phase at the bottom of the chamber. These agglomerations then move through the horizontal chamber with little effective redispersion. I have found that a vast improvement in dispersion results from orientation of the reaction chamber such that the direction of movement of the dispersion is the same as the direction of movement of the lighter phase within the dispersion. The lighter phase tends to move upwardly by virtue of its lower density. If the reaction chamber is designed such that movement of the dispersion is also upward there is less resultant phase separation, since the heavier phase tends to accompany the lighter phase in its upward movement. Retardation of phase separation prolongs the life of the dispersion and hence provides improved contact between the two phases.

The reaction chamber of my invention improves alkylate product quality over prior art alkylation reaction devices by providing a better acid-hydrocarbon dispersion therein. Better dispersion improves the acid phase's heat sink function, improves the uniformity of the acid to hydrocarbon ratio throughout the reaction chamber and reduces the fluoride content of the alkylate product. The acid phase acts as a heat sink in absorbing heat released by exothermic alkylation reactions. Better dispersion increases the effective area available for transfer of this heat and avoids the occurrence of "hot spots" within the reaction chamber which would promote undesirable reactions and undesirable by-products. Such by-products remain within and lower the quality of the alkylate product. Better dispersion improves the uniformity of the acid to hydrocarbon ratio throughout the reactor by reducing agglomerations of the individual phases. The fluoride content of the alkylate product is reduced when contact between acid and partially reacted hydrocarbons is improved, and this is effected by a prolongation of the life of the acid-hydrocarbon dispersion.

Referring now to the attached drawing, the latter shows an embodiment of my invention in which baffle means 10 provide changes in direction of an acid-hydrocarbon dispersion as it flows from the bottom to the top of vertically disposed, elongated vessel 1. In one embodiment of the present invention these baffle means may be plates having a section removed at alternate sides of chamber 1. If chamber 1 is cylindrical in cross section then the baffle means are in the form of discs with circular segment-shaped openings at alternate sides. The baffle means are disposed within chamber 1 substantially evenly spaced and perpendicular to its longitudinal axis such that the chamber volume is divided into compartments. A number of baffle means is installed which provides a pressure drop in vessel 1 of from 5 to 25 psi, and the resultant agitation aids in maintaining the acid-hydrocarbon dispersion. Interposed between baffle means 10, that is to say situated within separate compartments, is a plurality of reactant injection assemblies 11,12,13 and 14, each of which has a multiplicity of spray nozzles. Reactant sprays propagate in substantially all directions in the vicinities of assemblies 11,12,13 and 14. This is necessary to utilize as much as possible of the volume within the reactor which is available for dispersion of reactants and catalyst. Only a finite amount of space within each compartment is available for effecting contact between reactants and catalyst. In order to effectively use all of the space within each compartment the reactant sprays must be directed into substantially all portions of a compartment. Only in this way can full utilization of the total internal volume of the reactor be realized. In preferred embodiments of this invention the number of injection assemblies is from 2 to 6. The injection assemblies communicate with reactant conduits 4,5,6 and 7 through reactant stream inlet ports 19. Vessel 1 has end section 15 which contains means 17 for diverting coolant flow into heat exchange means 16 placed within chamber 1. In a preferred embodiment, the heat exchange means comprise a tube bundle. End section 15 also has coolant inlet 2 and coolant outlet 3. Vessel 1 is provided with catalyst inlet 9 and reaction products outlet 8.

In operation, catalyst enters the reaction chamber through conduit 9, passes in a serpentine path around baffles 10 and reactant injection assemblies 14,13,12 and 11 and exits the reaction chamber in conduit 8. In the vicinity of reactant injection assemblies 11,12,13 and 14 reactants are sprayed into the catalyst, creating an acid-hydrocarbon dispersion where reaction takes place. Upward movement of the dispersion tends to retard separation of the dispersed phases, and the multiple-stage injection of reactants effectively redisperses the phases at each stage. The acid-hydrocarbon dispersion, containing acid catalyst, reactants and reaction products exits vessel 1 in conduit 8 and proceeds to downstream processing steps where the alkylate product is recovered. The heat of reaction generated within the reaction cooler is withdrawn by heat exchange means 16 to maintain predetermined temperature conditions. In a preferred embodiment of my invention reactant injection assemblies 11,12,13 and 14 are horizontal pipes having multiplicities of spray nozzles which propagate sprays in all directions about the longitudinal axis of the pipes, as shown in the drawing.

Reasonable variation and modification are possible within the scope of the foregoing disclosure, the drawing, and the claims to the invention without departing from the spirit thereof.

I claim as my invention:

1. An acid-catalyzed alkylation reaction chamber which comprises, in combination:
    a. a vertically-disposed, elongated cylindrical vessel having internal heat removal means;
    b. an acid inlet port at the lower end of said vessel and a reaction product outlet port at the upper end of said vessel;
    c. a plurality of vertically spaced reactant stream inlet ports disposed along said vessel between said acid inlet port and said reaction product outlet port;
    d. a plurality of vertically spaced baffles within said vessel perpendicular to the longitudinal axis thereof, said baffles dividing the inner volume of said vessel into compartments, and said baffles having circular segment-shaped openings at alternate sides of said vessel to provide a serpentine flow of liquid upwardly through the vessel; and
    e. a plurality of reactant injection assemblies within said vessel, each disposed between a pair of adjacent baffles, within a compartment, and communicating with one of said reactant stream inlet ports, said injection assemblies comprising spray nozzles oriented to direct spray into substantially all portions of said compartment in which said injection assembly is situated.

2. The reaction chamber of claim 1 further characterized in the provision of two to six of said reactant injection assemblies.

3. The combination of claim 1 further characterized in that said baffles are substantially evenly spaced between said acid inlet port and said product outlet port.

* * * * *